(12) United States Patent
Toda

(10) Patent No.: US 6,640,631 B1
(45) Date of Patent: Nov. 4, 2003

(54) SYSTEM AND MEASURING SOUND VELOCITY IN MATERIAL

(76) Inventor: Kohji Toda, 1-49-18 Futaba, Yokosuka 239-0814 (JP)

( * ) Notice: Subject to any disclaimer, the term of this patent is extended or adjusted under 35 U.S.C. 154(b) by 0 days.

(21) Appl. No.: 10/153,565

(22) Filed: May 20, 2002

(51) Int. Cl.[7] .......................... G01N 29/18; G01N 29/24
(52) U.S. Cl. ............................ 73/597; 73/602; 73/628; 310/334; 367/164; 600/437
(58) Field of Search .......................... 73/597, 598, 625, 73/626, 627, 602, 628; 600/437, 442, 447, 448, 459; 310/334, 336, 337; 367/157, 164

(56) References Cited

U.S. PATENT DOCUMENTS

| | | | | |
|---|---|---|---|---|
| 4,296,348 A | * | 10/1981 | Toda | 310/334 |
| 4,375,767 A | * | 3/1983 | Magori | 73/861.18 |
| 4,399,387 A | * | 8/1983 | Kohji | 310/334 |
| 4,437,033 A | * | 3/1984 | Diepers | 310/334 |
| 4,448,075 A | * | 5/1984 | Takemura et al. | 73/626 |
| 5,164,627 A | * | 11/1992 | Popek | 310/313 B |
| 6,317,389 B1 | * | 11/2001 | Toda | 367/164 |
| 6,360,611 B1 | * | 3/2002 | Toda | 73/651 |
| 6,393,920 B1 | * | 5/2002 | Toda | 73/721 |
| 6,564,649 B1 | * | 5/2003 | Toda | 73/861.26 |

* cited by examiner

Primary Examiner—Hezron Williams
Assistant Examiner—Rose M. Miller

(57) ABSTRACT

A system for measuring sound velocity in material comprises a piezoelectric substrate, first- and second comb-shaped electrodes, and a counter electrode in contact with a surface-part of a material. When input electric signals $E_i$ having carrier frequencies $f_i$, respectively, are applied between the first comb-shaped electrode and the counter electrode in turn, longitudinal waves are radiated into the material. The longitudinal waves are reflected at the opposite surface-part of the material, and then, detected between the second comb-shaped electrode and the counter electrode as delayed electric signals $D_i$, respectively. The input electric signals $E_i$ and the delayed electric signals $D_i$ interfere respectively, so that respective interference signals $R_i$ occur. A sound velocity V in the material is estimated from the interference signals $R_i$.

21 Claims, 18 Drawing Sheets finger overlap-zone finger overlap-zone

SYSTEM AND MEASURING SOUND VELOCITY IN MATERIAL

BACKGROUND OF THE INVENTION

1. Field of the Invention

The present invention relates to a system for measuring a sound velocity in material by means of using a piezoelectric substrate, an interdigital arrangement of two comb-shaped electrodes formed on an upper end surface of the piezoelectric substrate, a counter electrode formed on a lower end surface of the piezoelectric substrate, a frequency-sweep oscillator and a frequency analyzer.

2. Description of the Prior Art

In recent years, ultrasonic techniques for measuring the sound velocity in a liquid are essential in the field of biophysics and medical science as well as physical acoustics, industry, physical chemistry, and others. A thickness mode piezoelectric transducer with parallel plate-like electrodes is commonly used for this purpose. Such a conventional type of transducer needs, for example, a circulator in order to separate a delayed electric signal from an input electric signal, because the conventional type of transducer is used both as input- and output electrodes. Accordingly, such the conventional type of transducer has a difficulty in quick response measurement, and a complicated circuit-construction.

On the other hand, an interdigital transducer on the piezoelectric substrate operates at a liquid-solid boundary as a leaky wave transducer for bulk wave radiation into the liquid. The leaky SAW traveling on a sufficiently thick substrate compared with the wavelength has only one mode without velocity dispersion. Such the interdigital transducer for the leaky SAW has a difficulty in making the radiation angle vertical, so that has a difficulty in measurement accuracy, and stable operation.

SUMMARY OF THE INVENTION

An object of the, present invention is to provide a system for measuring a sound velocity in material capable of making an interdigital transducer act as a thickness mode transducer.

Another object of the present invention is to provide a system for measuring a sound velocity in material operating with a quick response.

Another object of the present invention is to provide a system for measuring a sound velocity in material need not a circulator, and so on.

Another object of the present invention is to provide a system for measuring a sound velocity in material capable of making the radiation angle vertical.

Another object of the present invention is to provide a system for measuring a sound velocity in material capable of low electric power consumption.

Another object of the present invention is to provide a system for measuring a sound velocity in material capable of measuring the sound velocity in cellular tissue.

Another object of the present invention is to provide a system for measuring a sound velocity in material excellent in durability and manufacturing.

Another object of the present invention is to provide a system for measuring a sound velocity in material, which is not affected by a change in circumstances, for example, a change in temperature.

A still other object of the present invention is to provide a system for measuring a sound velocity in material easy in use and having a small size which is very light in weight and has a simple structure.

According to one aspect of the present invention there is provided a system for measuring a sound velocity in material comprising a piezoelectric substrate, first- and second comb-shaped electrodes formed on an upper end surface of the piezoelectric substrate, a counter electrode formed on a lower end surface of the piezoelectric substrate, a frequency-sweep oscillator generating input electric signals $E_i$ (i=1, 2, . . . , n) with carrier frequencies $f_i$ (i=1, 2, . . . , n), respectively, and a frequency analyzer. The counter electrode is in contact with a surface-part of a material. The first- and second comb-shaped electrodes form an interdigital arrangement.

When the input electric signals $E_i$ are applied between the first comb-shaped electrode and the counter electrode in turn, longitudinal waves are radiated into the material along the direction vertical to the lower end surface of the piezoelectric substrate. If the longitudinal waves are reflected at the opposite surface-part of the material, reflected longitudinal waves are detected between the second comb-shaped electrode and the counter electrode as delayed electric signals $D_i$ (i=1, 2, . . . , n), respectively. On the other hand, electrical coupled-signals $C_i$ (i=1, 2, . . . , n) from the input electric signals $E_i$, respectively, are also detected between the second comb-shaped electrode and the counter electrode. The electrical coupled-signals $C_i$ and the delayed electric signals $D_i$ interfere, respectively, so that respective interference signals $R_i$ (i=1, 2, . . . , n) occur. Tracing a dependence of respective amplitudes of the interference signals $R_i$ on the carrier frequencies $f_i$ provides a frequency periodicity $\Delta f$. Thus, a sound velocity V in the material is calculated from the product of the frequency periodicity $\Delta f$ and twice a distance Z between the piezoelectric substrate and the opposite surface-part of the material.

According to another aspect of the present invention there is provided a system for measuring a sound velocity in material further comprising a reflector, which is parallel with the lower end surface of the piezoelectric substrate and in contact with the opposite surface-part of the material.

According to another aspect of the present invention there is provided a system for measuring a sound velocity in material, wherein the ratio of the interdigital periodicity of the interdigital arrangement to the thickness of the piezoelectric substrate is smaller than four times the ratio of the longitudinal wave velocity in the material to the longitudinal wave velocity in the piezoelectric substrate.

According to another aspect of the present invention there is provided a system for measuring a sound velocity in material, wherein increasing the number of electrode-finger pairs in the interdigital arrangement makes the directionality of the longitudinal waves sharper under a condition that the total amount of all the finger-areas of the first comb-shaped electrode is constant.

According to another aspect of the present invention there is provided a system for measuring a sound velocity in material, wherein the material is a liquid matter.

According to another aspect of the present invention there is provided a system for measuring a sound velocity in material, wherein the material is a cellular tissue.

According to another aspect of the present invention there is provided a system for measuring a sound velocity in material further comprising a polymer film, with which the lower end surface of the counter electrode is coated.

According to another aspect of the present invention there is provided a system for measuring a sound velocity in material comprising a first piezoelectric, substrate, a first interdigital arrangement of two comb-shaped. electrodes formed on a lower end surface of the first piezoelectric substrate, a second piezoelectric substrate, a second interdigital arrangement of two comb-shaped electrodes formed on an upper end surface of the second piezoelectric substrate, a counter electrode cemented between the first- and second piezoelectric substrates, a frequency-sweep oscillator generating input electric signals $E_i$ (i=1, 2, . . . , n) with carrier frequencies $f_i$ (i=1, 2, . . . , n), respectively, and a frequency analyzer. A lower end surface of the first interdigital arrangement is in contact with a surface-part of a material.

When the input electric signals $E_i$ are applied between one of the two comb-shaped electrodes in the first interdigital arrangement and the counter electrode in turn, longitudinal waves are radiated into the material along the direction vertical to the lower end surface of the first piezoelectric substrate. If the longitudinal waves are reflected at the opposite surface-part of the material, reflected longitudinal waves are detected between one of the two comb-shaped electrodes in the second interdigital arrangement and the counter electrode as delayed electric signals $D_i$ (i=1, 2, . . . , n), respectively. On the other hand, electrical coupled-signals $C_i$ (i=1, 2, . . . , n) from the input electric signals $E_i$, respectively, are also detected between the one of the two comb-shaped electrodes in the second interdigital arrangement and the counter electrode. The electrical coupled-signals $C_i$ and the delayed electric signals $D_i$ interfere, respectively, so that respective interference signals $R_i$ (i=1, 2, . . . , n) occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$.

According to another aspect of the present invention there is provided a system for measuring a sound velocity in material, wherein the finger direction of the second interdigital arrangement is orthogonal to that of the first interdigital arrangement.

According to another aspect of the present invention there is provided a system for measuring a sound velocity in material, wherein the finger width in the one of the two comb-shaped electrodes in the first interdigital. arrangement is wider than that in the other of the two comb-shaped electrodes in the first interdigital arrangement, and the finger width in the one of the two comb-shaped electrodes in the second interdigital arrangement is wider than that in the other of the two comb-shaped electrodes in the second interdigital arrangement.

According to another aspect of the present invention there is provided a system for measuring a sound velocity in material further comprising a reflector, which is parallel with the lower end surface of the first piezoelectric substrate and in contact with the opposite surface-part of the material.

According to another aspect of the present invention there is provided a system for measuring a sound velocity in material, wherein the ratio of the interdigital periodicity of the first interdigital arrangement to the thickness of the first piezoelectric substrate is smaller than four times the ratio of the longitudinal wave velocity in the material to the longitudinal wave velocity in the first piezoelectric substrate.

According to another aspect of the present invention there is provided a system for measuring a sound velocity in material, wherein increasing the number of electrode-finger pairs in the first interdigital arrangement makes the directionality of the longitudinal waves sharper under a condition that the total amount of all the finger-areas of the one of the two comb-shaped electrodes in the first interdigital arrangement is constant.

According to another aspect of the present invention there is provided a system for measuring a sound velocity in material comprising a first piezoelectric substrate, a first comb-shaped electrode formed on a lower end surface of the first piezoelectric substrate, a second piezoelectric substrate, a second comb-shaped electrode formed on an upper end surface of the second piezoelectric substrate, a counter electrode cemented between the first- and second piezoelectric substrates, a frequency-sweep oscillator generating input electric signals $E_i$ (i=1, 2, . . . , n) with carrier frequencies $f_i$ (i=1, 2, . . . , n), respectively, and a frequency analyzer. A lower end surface of the first comb-shaped electrode is in contact with a surface-part of a material.

When the input electric signals $E_i$ are applied between the first comb-shaped electrode and the counter electrode in turn, longitudinal waves are radiated into the material along the direction vertical to the lower end surface of the first piezoelectric substrate. If the longitudinal waves are reflected at the opposite surface-part of the material, reflected longitudinal waves are detected between the second comb-shaped electrode and the counter electrode as delayed electric signals $D_i$ (i=1, 2, . . . , n), respectively. On the other hand, electrical coupled-signals $C_i$ (i=1, 2, . . . , n) from the input electric signals $E_i$, respectively, are also detected between the second comb-shaped electrode and the counter electrode. The electrical coupled-signals $C_i$ and the delayed electric signals $D_i$, interfere, respectively, so that respective interference signals $R_i$ (i=1, 2, . . . , n) occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$.

According to another aspect of the present invention there is provided a system for measuring a sound velocity in material, wherein the finger direction of the second comb-shaped electrode is orthogonal to that of the first comb-shaped electrode.

According to another aspect of the present invention there is provided a system for measuring a sound velocity in material, wherein the ratio of the interdigital periodicity of the first comb-shaped electrode to the thickness of the first piezoelectric substrate is smaller than four times the ratio of the longitudinal wave velocity in the material to the longitudinal wave velocity in the first piezoelectric substrate.

According to other aspect of the present invention there is provided a system for measuring a sound velocity in material, wherein increasing the number of electrode-finger pairs in the first comb-shaped electrode makes the directionality of the longitudinal waves sharper under a condition that the total amount of all the finger-areas of the first comb-shaped electrode is constant.

According to a further aspect of the present invention. there is provided a system for measuring a sound velocity in material, wherein the input electric signals $E_i$ is accompanied by alternating current bias-signals $S_i$ (i=1, 2, . . . , n) with the carrier frequencies $f_i$, respectively. In this case, not the electrical coupled-signals $C_i$, but the alternating current bias-signals $S_i$, and the delayed electric signals $D_i$ interfere, respectively, so that the interference signals $R_i$ occur.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
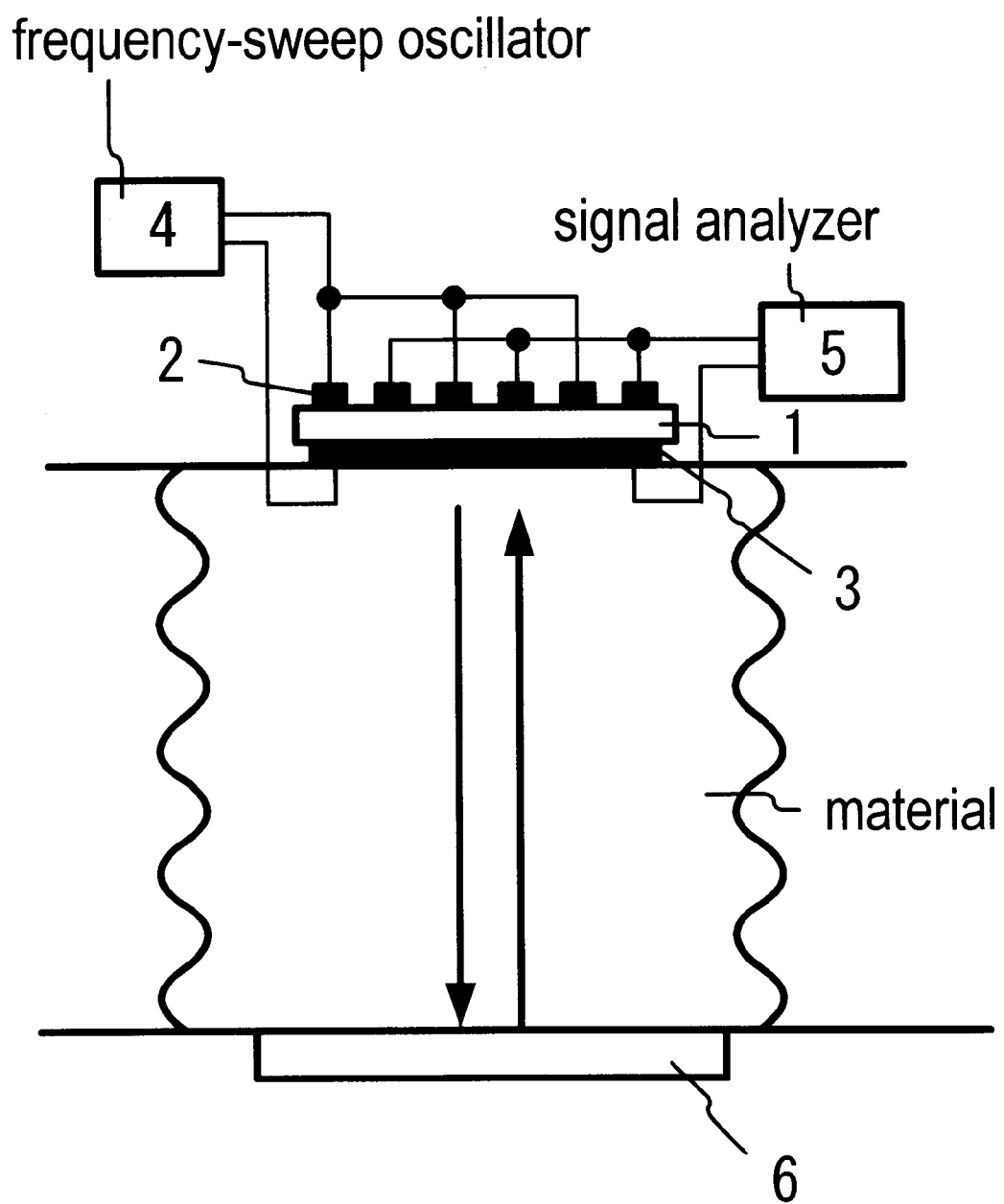
FIG. 1 shows a schematic illustration of a system for measuring sound velocity in material according to a first embodiment of the present invention.

FIG. 1 shows a schematic illustration of a system for measuring sound velocity in material according to a first embodiment of the present invention. The system for measuring sound velocity in material comprises piezoelectric substrate 1, interdigital arrangement 2 of two comb-shaped electrodes (2A and 2B), counter electrode 3, frequency-sweep oscillator 4, frequency analyzer 5, and reflector 6. Piezoelectric substrate 1 is made of a piezoelectric ceramic plate with a thickness (T) of 500 μm, and the polarization axis thereof is parallel to the thickness direction thereof. Interdigital arrangement 2, made of an aluminum thin film, is formed on an upper end surface of piezoelectric substrate 1. Counter electrode 3, made of an aluminum thin film, is formed on a lower end. surface of piezoelectric substrate 1, and in contact with a material through the lower end surface of counter electrode 3. Reflector 6 is arranged to be parallel with the lower end surface of piezoelectric substrate 1, and in contact with the opposite surface-part of the material through the upper end surface of reflector 6. Thus, the system for measuring sound velocity in material in FIG. 1 has a small size, which is very light in weight and has a simple structure.

Figure 2:
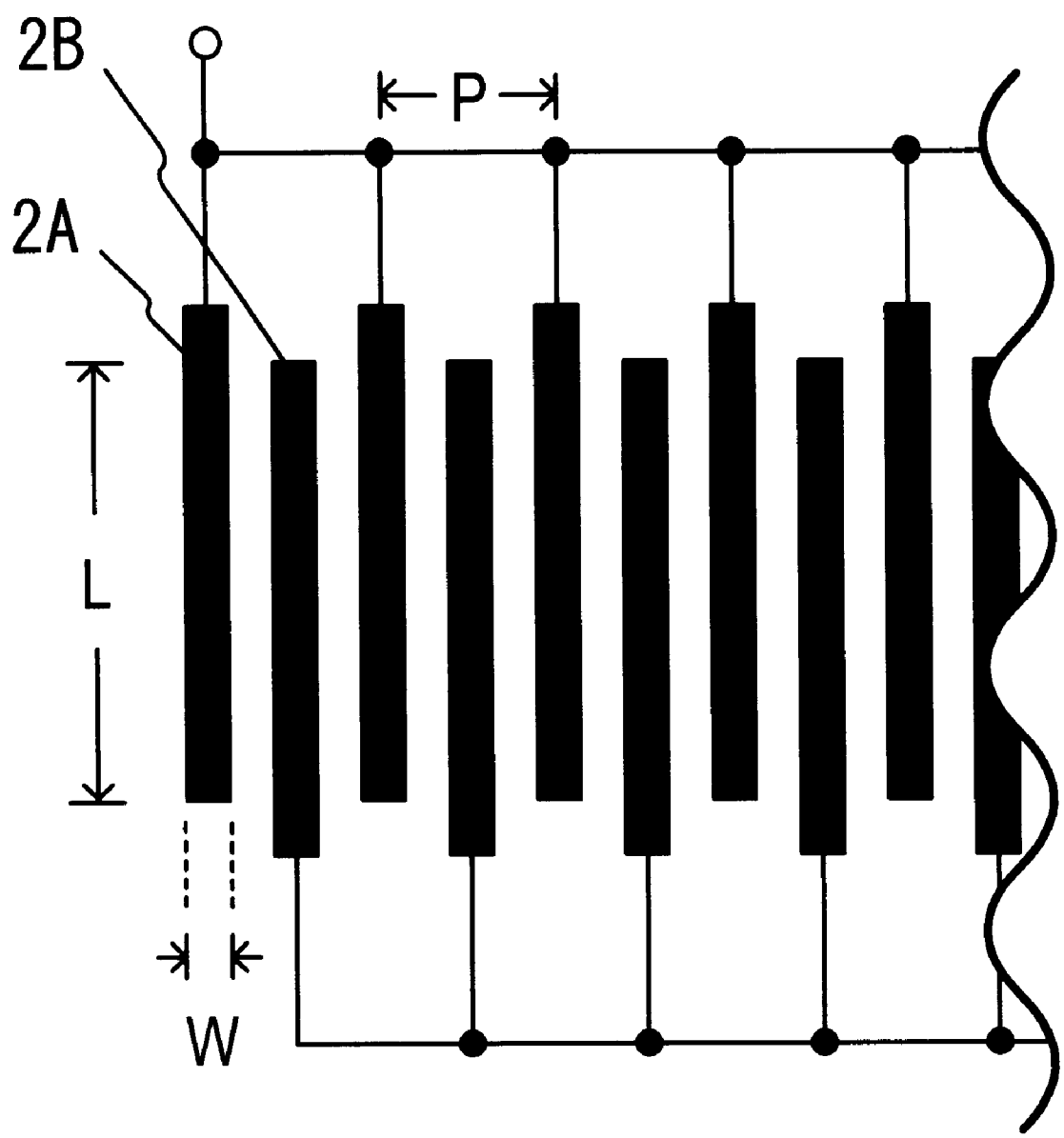
FIG. 2 shows a fragmentary top plan view of interdigital arrangement 2.

FIG. 2 shows a fragmentary top plan view of interdigital arrangement 2. Interdigital arrangement 2 has fifteen electrode-finger pairs, a finger-overlap length (L) of 5 mm, a finger width (W) of 75 μm, and an interdigital periodicity (P) of 300 μm. Interdigital arrangement 2 is composed of first comb-shaped electrode 2A and second comb-shaped electrode 2B.

In the system for measuring sound velocity in material in FIG. 1, if input electric signals $E_i$ (i=1, 2, . . . , n) from frequency-sweep oscillator 4 are applied between first comb-shaped electrode 2A and counter electrode 3 in turn, longitudinal waves along the direction vertical to the lower end surface of piezoelectric substrate 1 are radiated into the material through a surface-part of the material. In this time, the input electric signals $E_i$ have carrier frequencies $f_i$ (i=1, 2, . . . , n), respectively.

If the material is water, the longitudinal wave velocity in water ($V_w$) is approximately 1,500 m/s. On the other hand, the longitudinal wave velocity in piezoelectric substrate 1 ($V_s$) is 4,500 m/s. Thus, the ratio of the $V_w$ value to the $V_s$ value, that is 1,500/4,500, is approximately 0.333. The ratio of the interdigital periodicity (P) of interdigital arrangement 2 to the thickness (T) of piezoelectric substrate 1, that is 300/500, is 0.6, which is still smaller than four times the ratio of the $V_w$ value to the $V_s$ value. Under such a condition of $P/T<4V_w/V_s$, the longitudinal waves along the direction vertical to the lower end surface of piezoelectric substrate 1 are effectively radiated into water. In the same way, the longitudinal waves are effectively radiated into, for example, a cellular tissue.

If the longitudinal waves are reflected at the opposite surface-part of the material, or at reflector 6 as shown in FIG. 1, reflected longitudinal waves are detected between second comb-shaped electrode 2B and counter electrode 3 as delayed electric signals $D_i$ (i=1, 2, . . . , n), respectively. On the other hand, electrical coupled-signals $C_i$ (i=1, 2, . . . , n) from the input electric signals $E_i$, respectively, are also detected between second comb-shaped electrode 2B and counter electrode 3. The electrical coupled-signals $C_i$ and the delayed electric signals $D_i$ interfere, respectively, so that respective interference signals $R_i$ (i=1, 2, . . . , n) occur. Tracing a dependence of respective amplitudes of the interference signals $R_i$ on the carrier frequencies $f_i$ provides a frequency periodicity Δf. Thus, a sound velocity V in the material is calculated from the product of the frequency periodicity Δf and twice a distance Z between piezoelectric substrate 1 and the opposite surface-part of the material, that is, V=2ZΔf.

In the system for measuring sound velocity in material in FIG. 1, if the input electric signals $E_i$ accompanied by alternating current bias-signals $S_i$ (i=1, 2, . . . , n) with the carrier frequencies $f_i$, respectively, are applied between first comb-shaped electrode 2A and counter electrode 3 in turn, longitudinal waves along the direction vertical to the lower end surface of piezoelectric substrate 1 are radiated into the material. If the longitudinal waves are reflected at reflector 6 as shown in FIG. 1, reflected longitudinal waves are detected between second comb-shaped electrode 2B and counter electrode 3 as the delayed electric signals $D_i$, respectively. The alternating current bias-signals $S_i$ and the delayed electric signals $D_i$ interfere respectively with each other, so that the interference signals $R_i$ occur. Tracing a dependence of respective amplitudes of the interference signals $R_i$ on the carrier frequencies $f_i$ provides a frequency periodicity $\Delta f$. Thus, a sound velocity V in the material is calculated from the product of the frequency periodicity $\Delta f$ and twice a distance Z between piezoelectric substrate 1 and reflector 6, that is, $V=2Z\Delta f$. The use of the input electric signals $E_i$ accompanied by the alternating current bias-signals $S_i$ enables a more stable operation.

Figure 3:
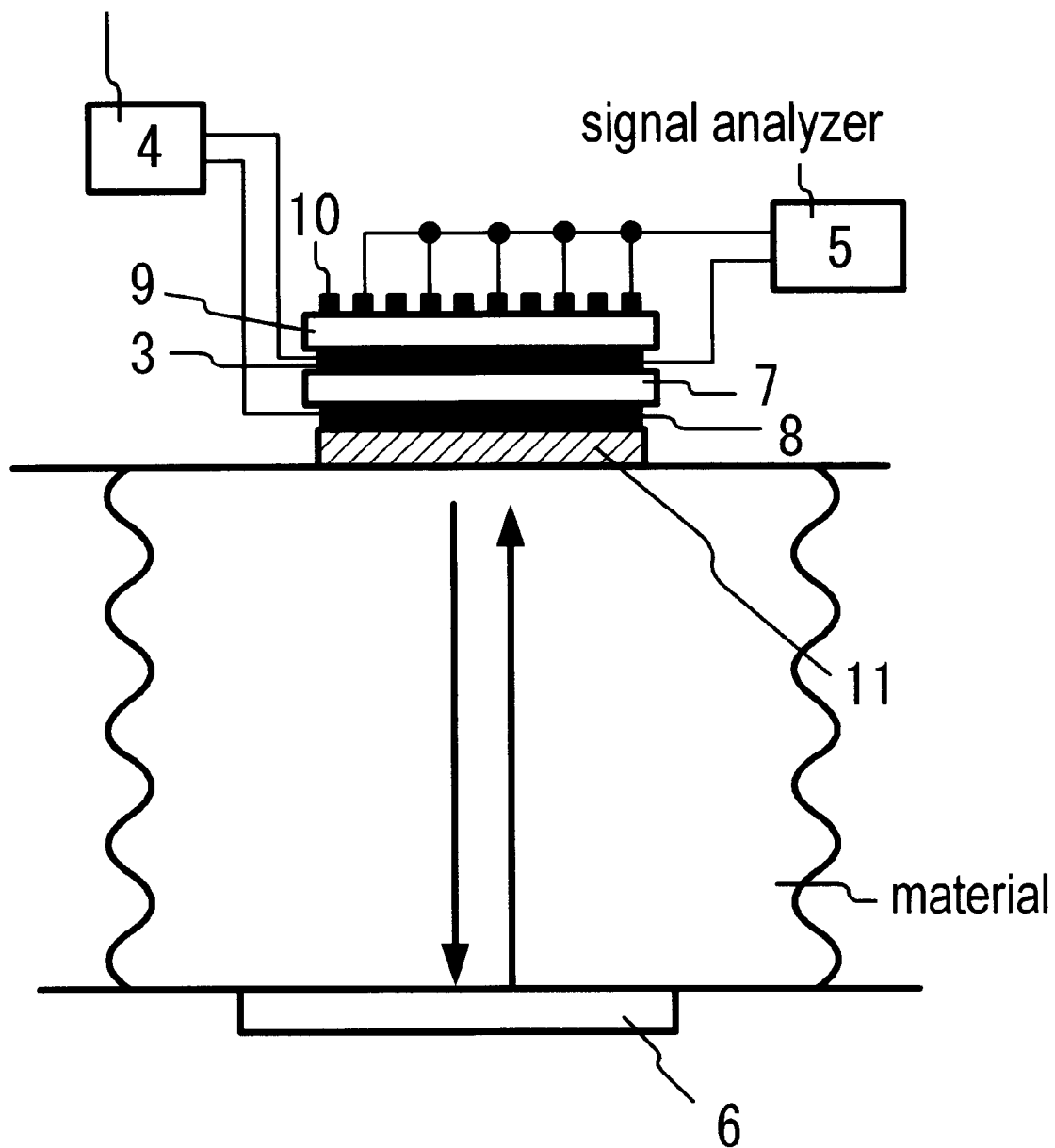
FIG. 3. shows a schematic illustration of a system for measuring sound velocity in material according to a second embodiment of the present invention.

FIG. 3 shows a schematic illustration of a system for measuring sound velocity in material according to a second embodiment of the present invention. The system for measuring sound velocity in material comprises first piezoelectric substrate 7, first interdigital arrangement 8 of two comb-shaped electrodes (8A and 8B), second piezoelectric substrate 9, second interdigital arrangement 10 of two comb-shaped electrodes (10A and 10B), counter electrode 3, frequency-sweep oscillator 4, frequency analyzer 5, reflector 6, and silicone rubber 11. First interdigital arrangement 8 is formed on the lower end surface of first piezoelectric substrate 7. Second interdigital arrangement 10 is formed on the upper end surface of second piezoelectric substrate 9. Counter electrode 3 is cemented between first piezoelectric substrate 7 and second piezoelectric substrate 9, which are made of the same materials as piezoelectric substrate 1, and have the same sizes as piezoelectric substrate 1. The lower end surface of first piezoelectric substrate 7 is coated with silicone rubber 11, which is in contact with a surface-part of a material. Reflector 6 is arranged to be parallel with the lower end surface of first piezoelectric substrate 7, and in contact with the opposite surface-part of the material through the upper end surface of reflector 6.

Figure 4:
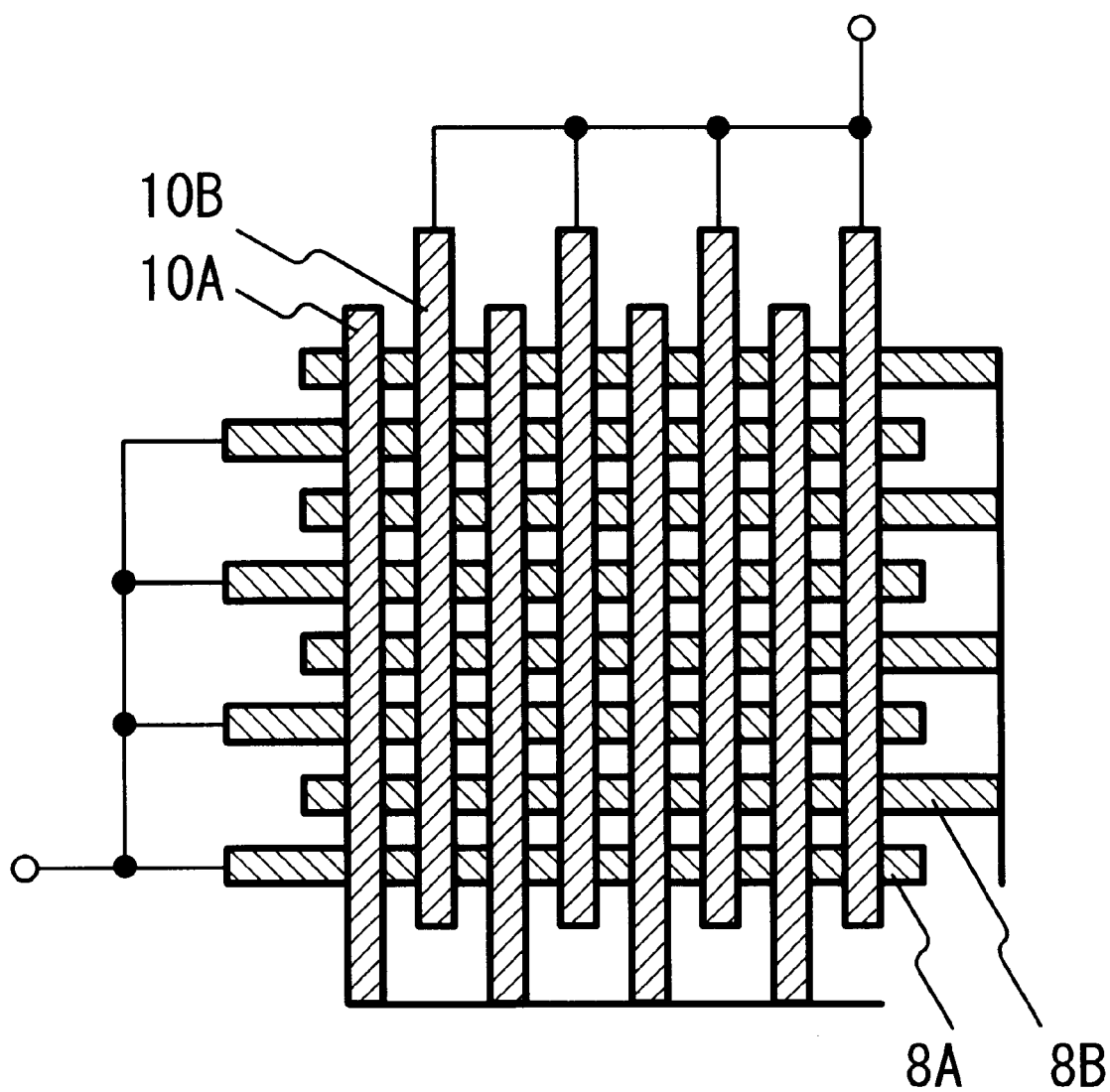
FIG. 4 shows a schematic illustration of first interdigital arrangement 8 and second interdigital arrangement 10 in the system for measuring sound velocity in material in FIG. 3.

FIG. 4 shows a schematic illustration of first interdigital arrangement 8 composed of first comb-shaped electrode 8A and second comb-shaped electrode 8B, and second interdigital arrangement 10 composed of first comb-shaped electrode 10A and second comb-shaped electrode 10B in the system for measuring sound velocity in material in FIG. 3. The finger direction of first interdigital arrangement 8 is orthogonal to that of second interdigital arrangement 10. First interdigital arrangement 8, made of an aluminum thin film, has twenty electrode-finger pairs, a finger-overlap length (L) of 5 mm, a finger width (W) of 57 $\mu$m, and an interdigital periodicity (P) of 225 $\mu$m. Second interdigital arrangement 10 is made of the same material and has the same construction pattern as first interdigital arrangement 8. First comb-shaped electrode 8A and second comb-shaped electrode 10B are connected with frequency-sweep oscillator 4 and frequency analyzer 5 in FIG. 3, respectively.

In the system for measuring sound velocity in material in FIG. 3, if the input electric signals $E_i$ from frequency-sweep oscillator 4 are applied between first comb-shaped electrode 8A and counter electrode 3 in turn, longitudinal waves along the direction vertical to the lower end surface of first piezoelectric substrate 7 are radiated into the material through silicone rubber 11. When the material is water, the ratio of the $V_w$ value to the $V_s$ value is approximately 0.333, as mentioned above. On the other hand, the ratio of the interdigital periodicity (P) of first interdigital arrangement 8 to the thickness (T) of first piezoelectric substrate 7, that is 225/500, is 0.45, which is still smaller than four times the ratio of the $V_w$ value to the $V_s$ value. Under such a condition of $P/T<4V_w/V_s$, the longitudinal waves along the direction vertical to the lower end surface of first piezoelectric substrate 7 are effectively radiated into water through silicone rubber 11. In addition, the directionality of the longitudinal waves is sharper than that of the longitudinal waves in FIG. 1. In other words, the smaller ratio P/T than the ratio $4V_w/V_s$, the sharper directionality.

If the longitudinal waves are reflected at reflector 6 as shown in FIG. 3, reflected longitudinal waves are detected between second comb-shaped electrode 10B and counter electrode. 3 as the delayed electric signals $D_i$, respectively. In this time, the directionality of the reflected longitudinal waves is sharper than that of the longitudinal waves radiated into the material, because the finger direction of first interdigital arrangement 8 is orthogonal to that of second interdigital arrangement 10. On the other hand, the electrical coupled-signals $C_i$ from the input electric signals $E_i$, respectively, are also detected between second comb-shaped electrode 10B and counter electrode 3. Thus, the electrical coupled-signals $C_i$ and the delayed electric signals $D_i$ interfere, respectively, so that the respective interference signals $R_i$ occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$ In addition, the sound velocity V is more precisely estimated than the system for measuring sound velocity in material in FIG. 1.

Figure 5:
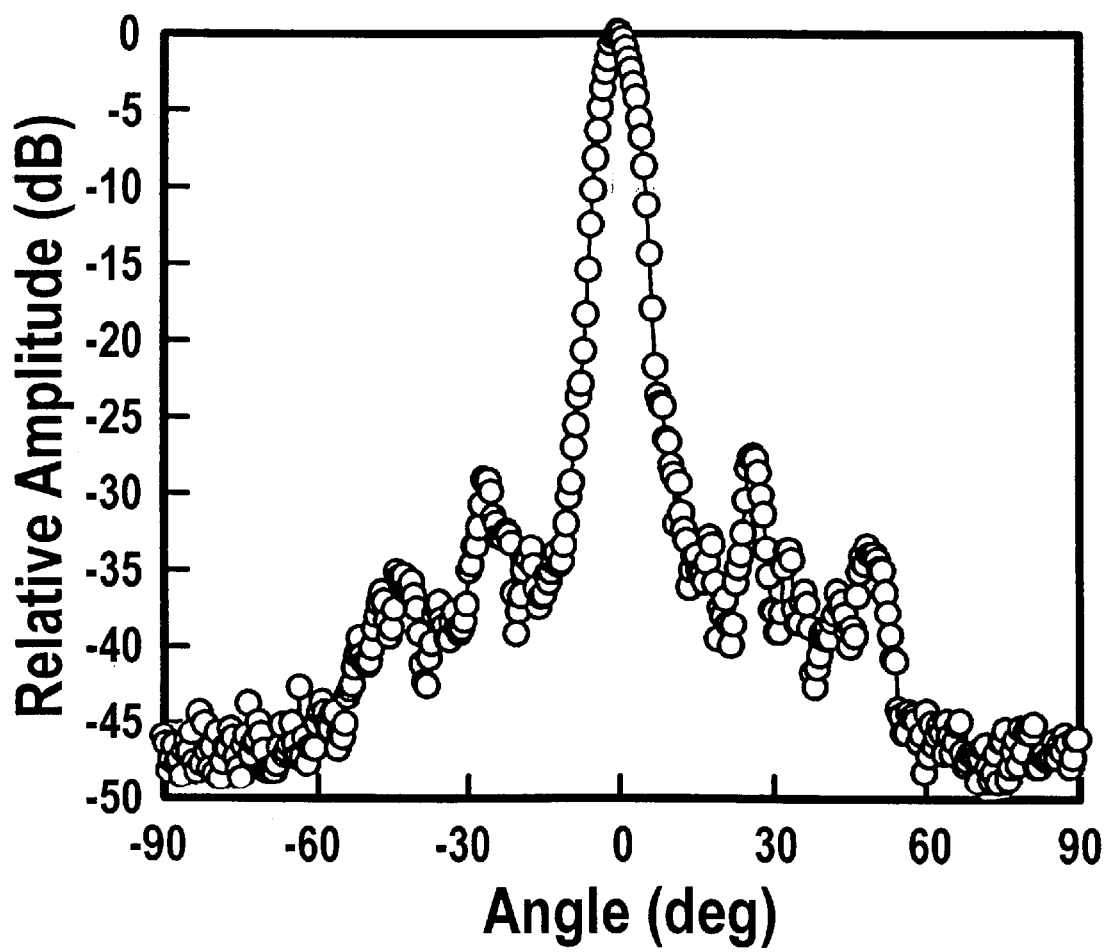
FIG. 5 shows a relationship between the relative amplitude and the radiation angle of the longitudinal waves into water from the system for measuring sound velocity in material in FIG. 3.

FIG. 5 shows a relationship between the relative amplitude and the radiation angle of the longitudinal waves into water from the system for measuring sound velocity in material in FIG. 3. It seems that there exists only the main lobe, because any grating lobe is suppressed. As a result, the use of first interdigital arrangement 8 enables only a vertical radiation to the lower end surface of first piezoelectric substrate 7 into water. Thus, the longitudinal waves are effectively radiated into, for example, a cellular tissue through a skin, along a vertical direction to the lower end surface of first piezoelectric substrate 7.

Figure 6:
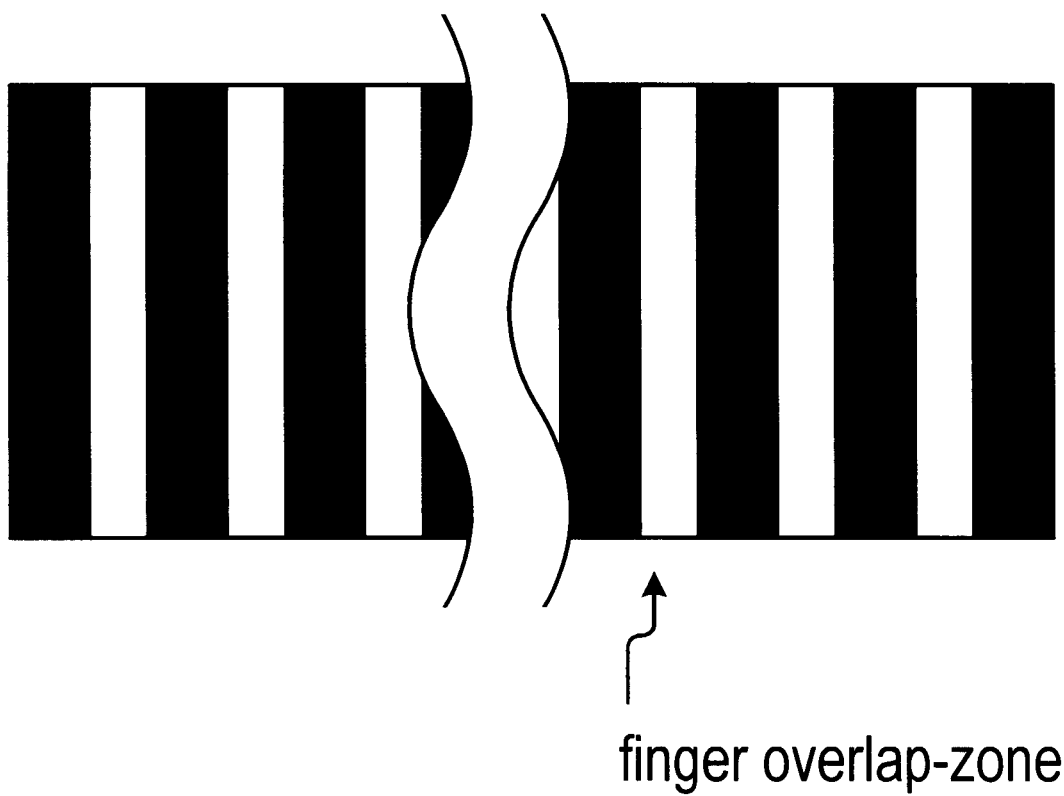
FIG. 6 shows a top plan view of the finger overlap-zone of interdigital arrangement 2.

FIG. 6 shows a top plan view of the finger overlap-zone of interdigital arrangement 2.

Figure 7:
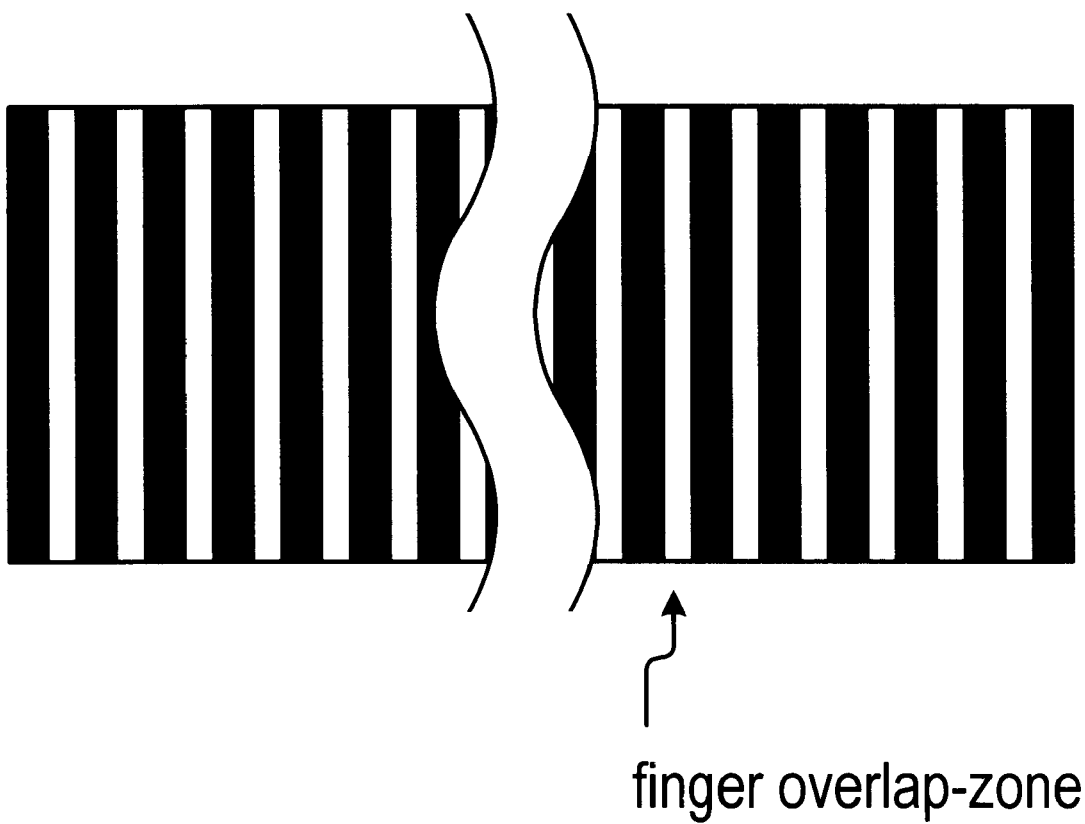
FIG. 7 shows a top plan view of the finger overlap-zone of first interdigital arrangement 8.

FIG. 7 shows a top plan view of the finger overlap-zone of first interdigital arrangement 8. The finger overlap-zone of first interdigital arrangement 8 and that of interdigital arrangement 2 are the same in size. In addition, the total amount of all the finger-areas of first. comb-shaped electrode 8A is the same as that of first comb-shaped electrode 2A.

A comparison between FIGS. 6 and 7 indicates that first interdigital arrangement 8 and interdigital arrangement 2 are different from each other with respect to the number of electrode-finger pairs, the finger width (W), and the interdigital periodicity (P). Actually, the number of electrode-finger pairs in first interdigital arrangement 8 is 4/3 times that in interdigital arrangement 2. At the same time, the interdigital periodicity (P) of first interdigital arrangement 8 is approximately 3/4 times that of interdigital arrangement 2, and the finger width (W) of first interdigital arrangement 8 is also 3/4 times that of interdigital arrangement 2. It is recognized that the use of first interdigital arrangement 8 causes a sharper directionality of the longitudinal wave than interdigital arrangement 2. This means that increasing the number of electrode-finger pairs suppresses the grating lobes still more under a condition that the total amount of all the finger-areas of the first comb-shaped electrode is constant. As a result, the number of electrode-finger pairs has influence on the directionality of the longitudinal waves into a material under the condition that the total amount of all the finger-areas of the first comb-shaped electrode is constant.

Figure 8:
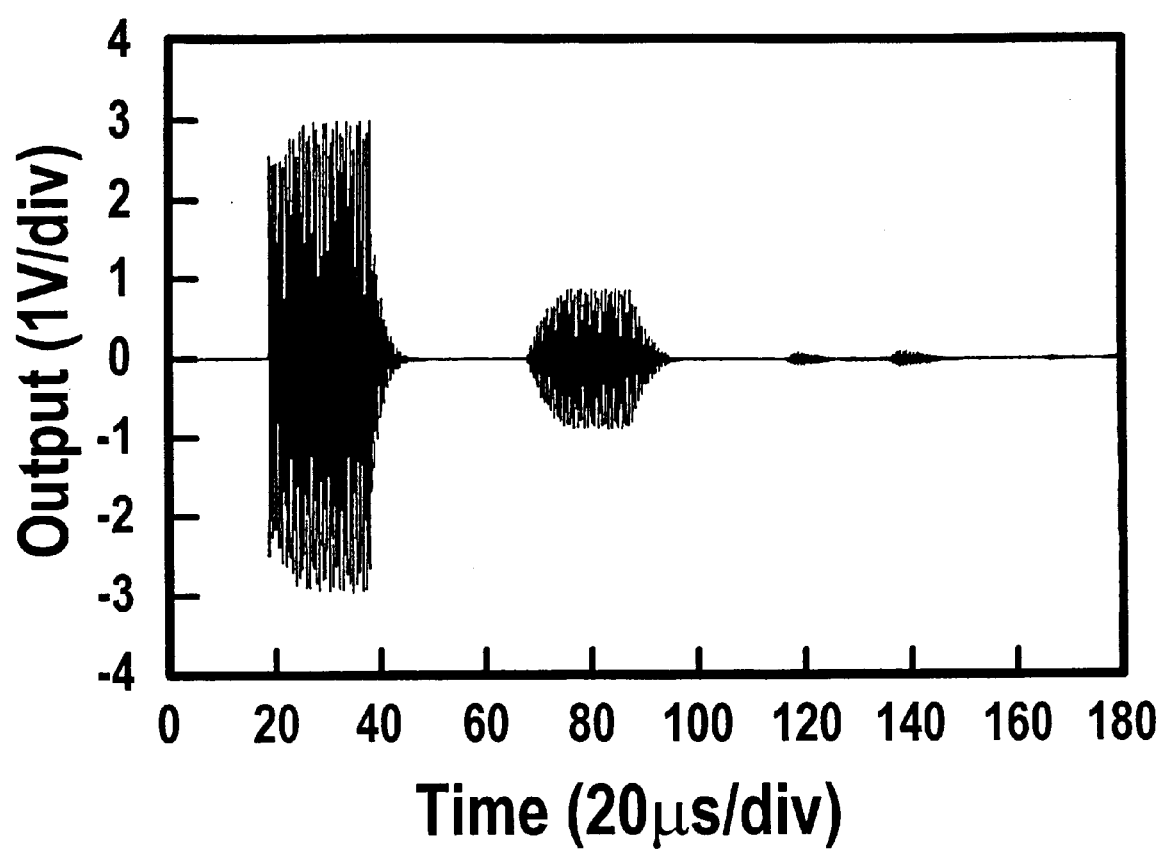
FIG. 8 shows an observed waveform at one of the carrier frequencies $f_i$ in the system for measuring sound velocity in material in FIG. 3.

FIG. 8 shows an observed waveform at one of the carrier frequencies $f_i$ in the system for measuring sound velocity in material in FIG. 3, in case that no interference signals $R_i$ appear because of a short time supply of the input electric signals $E_i$. It should be noticed that for the first time the left signal-part, that is, one of the electrical coupled-signals $C_i$ appears, and then, the right signal-part, that is, the corresponding one of the delayed electric signals $D_i$ appears.

Figure 9:
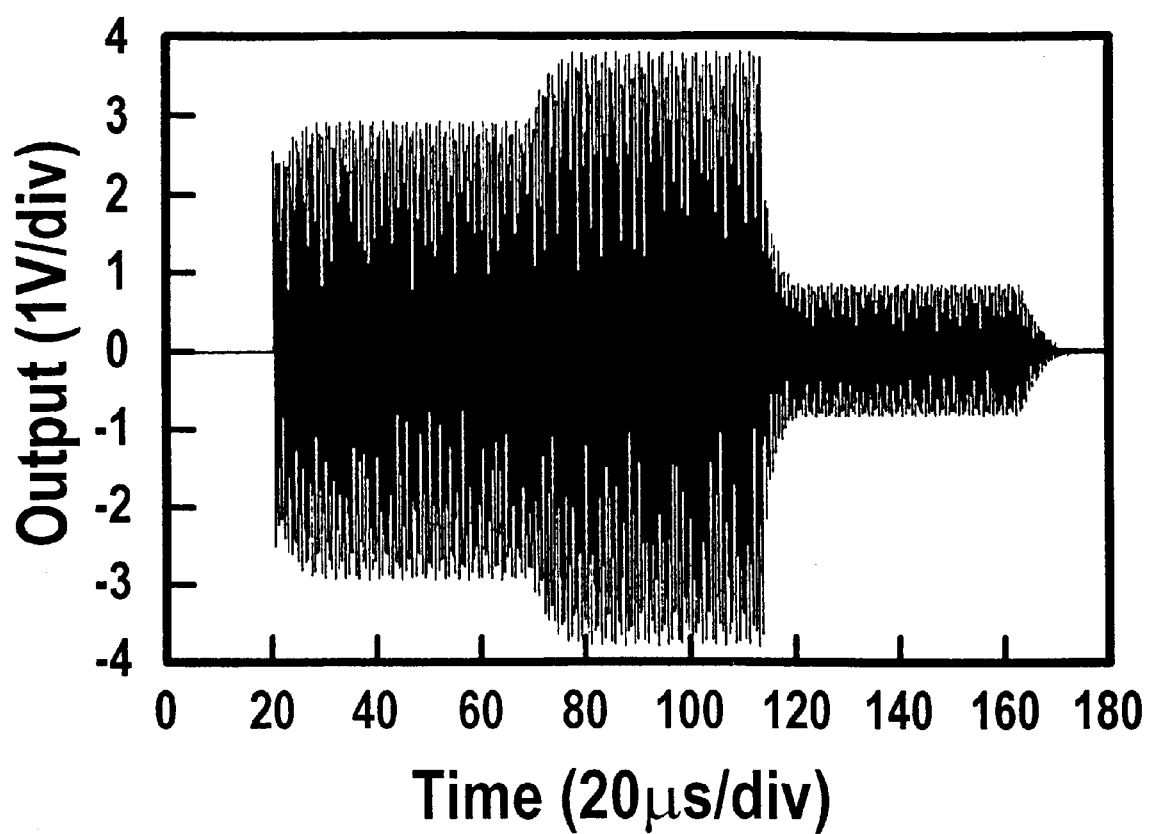
FIG. 9 shows an observed waveform at one of the carrier frequencies $f_i$ in the system for measuring sound velocity in material in FIG. 3.

FIG. 9 shows an observed waveform at one of the carrier frequencies $f_i$ in the system for measuring sound velocity in material in FIG. 3, in case that interference signals $R_i$ appear. It is noticed that one of the electrical coupled-signals $C_i$ and the corresponding one of the delayed electric signals $D_i$ interfere respectively, so that an overlapping signal, that is, the corresponding one of the interference signals $R_i$ with the corresponding one of the carrier frequencies $f_i$ occurs. In this time, the corresponding one of the interference signals $R_i$ has the maximum amplitude. For example, the electrical coupled-signals $C_3$ and the delayed electric signal $D_3$ interfere with each other, so that the interference signal $R_3$ with the carrier frequency $f_3$ occurs. Thus, the left-, right-, and middle signal-parts in FIG. 9 correspond, for example, the electrical coupled-signals $C_3$, the delayed electric signal $D_3$, and the interference signal $R_3$ with the carrier frequency $f_3$.

Figure 10:
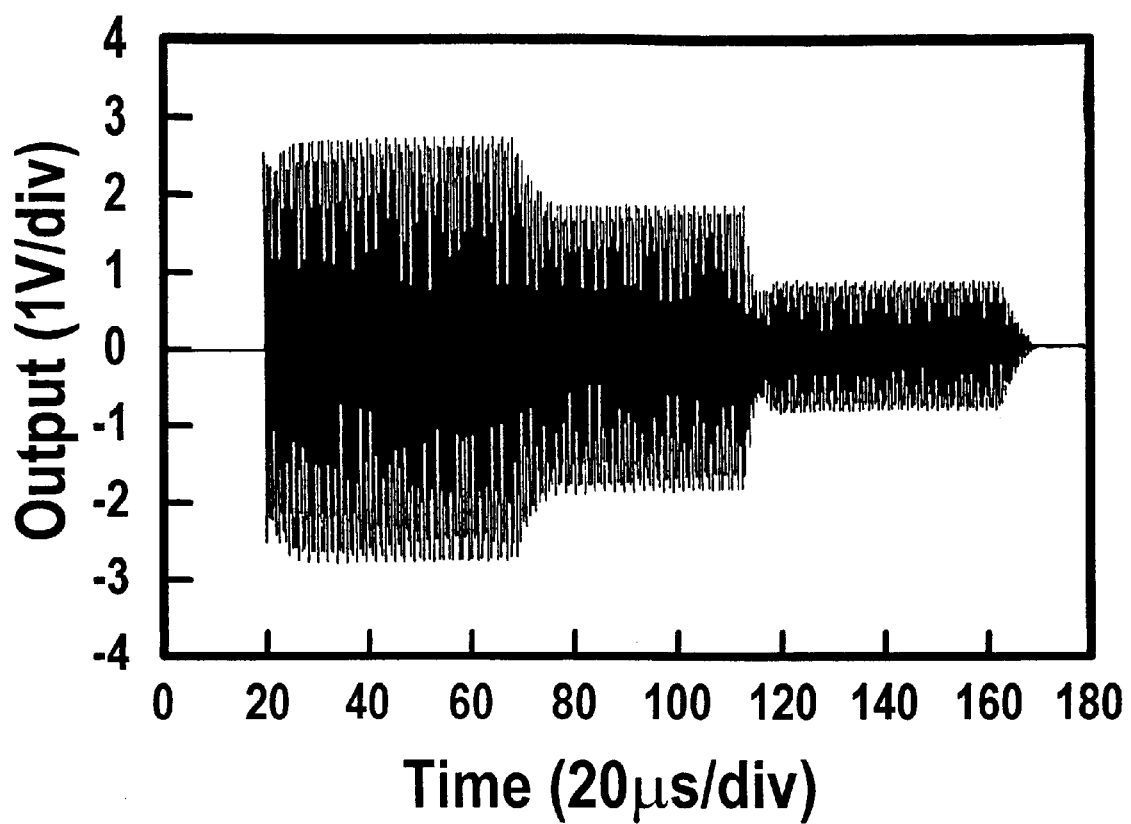
FIG. 10 shows an observed waveform at one of the carrier frequencies $f_i$ in the system for measuring sound velocity in material in FIG. 3.

FIG. 10 shows an observed waveform at one of the carrier frequencies $f_i$ in the system for measuring sound velocity in material in FIG. 3, in case that interference signals $R_i$ appear. In the same way as FIG. 9, one of the electrical coupled-signals $C_i$ and the corresponding one of the delayed electric signals $D_i$ interfere respectively, so that the corresponding one of the interference signals $R_i$ with the corresponding one of the carrier frequencies $f_i$ occurs. In this time, the corresponding one of the interference signals $R_i$ has the minimum amplitude in contrast to FIG. 9. Thus, the left-, right-, and middle signal-parts in FIG. 10 correspond, for example, the electrical coupled-signals $C_7$, the delayed electric signal $D_7$, and the interference signal $R_7$ with the carrier frequency $f_7$.

Figure 11:
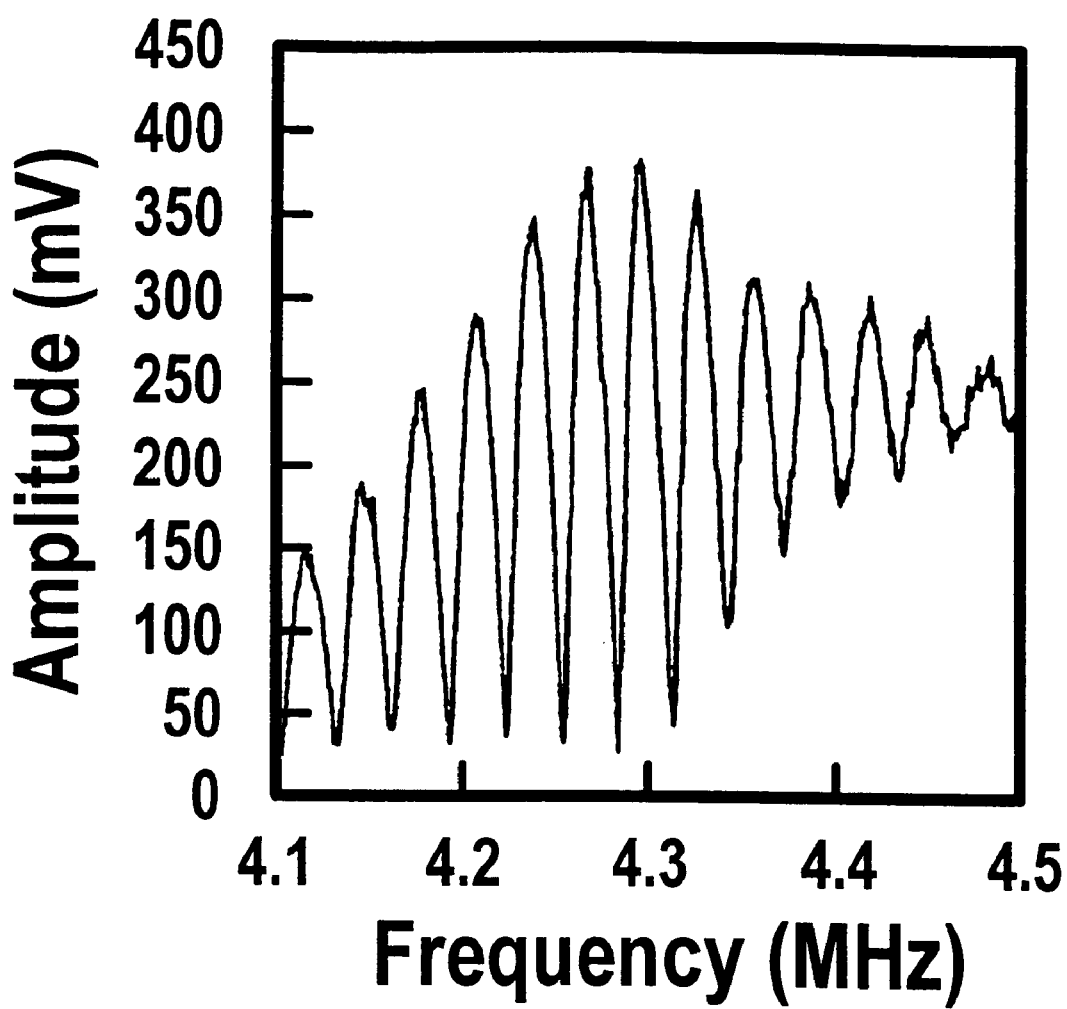
FIG. 11 shows a relationship between the amplitudes in voltage of the interference signals $R_i$ and the carrier frequency $f_i$.

FIG. 11 shows a relationship between the amplitudes in voltage of the interference signals $R_i$ and the carrier frequency $f_i$. In other words, a dependence of the amplitudes obtained from FIGS. 9 and 10, and other related data, on the carrier frequencies $f_i$ is traced in FIG. 11. A distance between two neighboring peak amplitudes corresponds to the frequency periodicity $\Delta f$.

Figure 12:
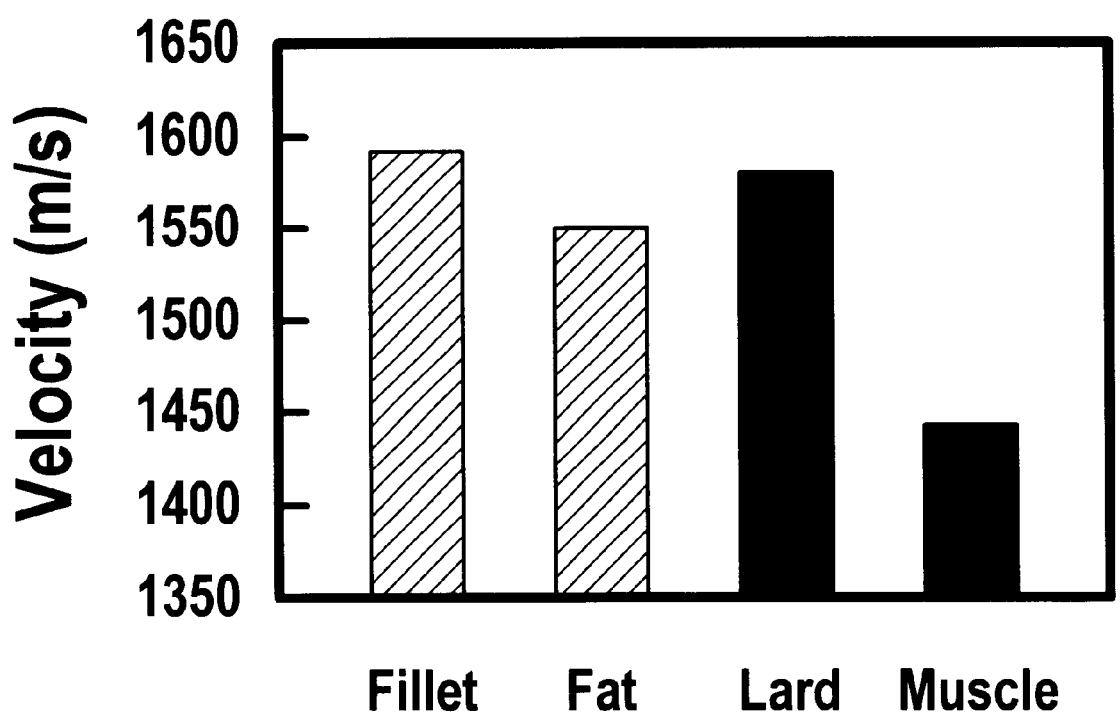
FIG. 12 shows a relationship between four kinds of parts a pork and the sound velocity V traveling therein.

FIG. 12 shows a relationship between four kinds of parts a pork and the sound velocity V traveling therein. The sound velocity V in fillet and that in fat are calculated from the equation, $V=2Z\Delta f$, in the system for measuring sound velocity in material in FIG. 3. The sound velocity V in muscle and that in lard are quoted from reference data. Thus, the sound velocity V in fillet, fat, muscle, or lard is 1592.6, 1551.4, 1580.0, or 1443.0 m/s, respectively. It should be noticed that the sound velocity V in fillet is higher than that in fat.

In the system for measuring sound velocity in material in FIG. 3, if the input electric signals $E_i$ accompanied by the alternating current bias-signals $S_i$ with the carrier frequencies $f_i$, respectively, are applied between first comb-shaped electrode 8A and counter electrode 3 in turn, longitudinal waves along the direction vertical to the lower end surface of first piezoelectric substrate 7 are radiated into the material through silicone rubber 11. If the longitudinal waves are reflected at reflector 6, reflected longitudinal waves are detected between second comb-shaped electrode 10B and counter electrode 3 as the delayed electric signals $D_i$, respectively. The alternating current bias-signals $S_i$ and the delayed electric signals $D_i$ interfere respectively with each other, so that respective interference signals $R_i$ occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$. The use of the input electric signals $E_i$ accompanied by the alternating current bias-signals $S_i$ enables a more stable operation.

Figure 13:
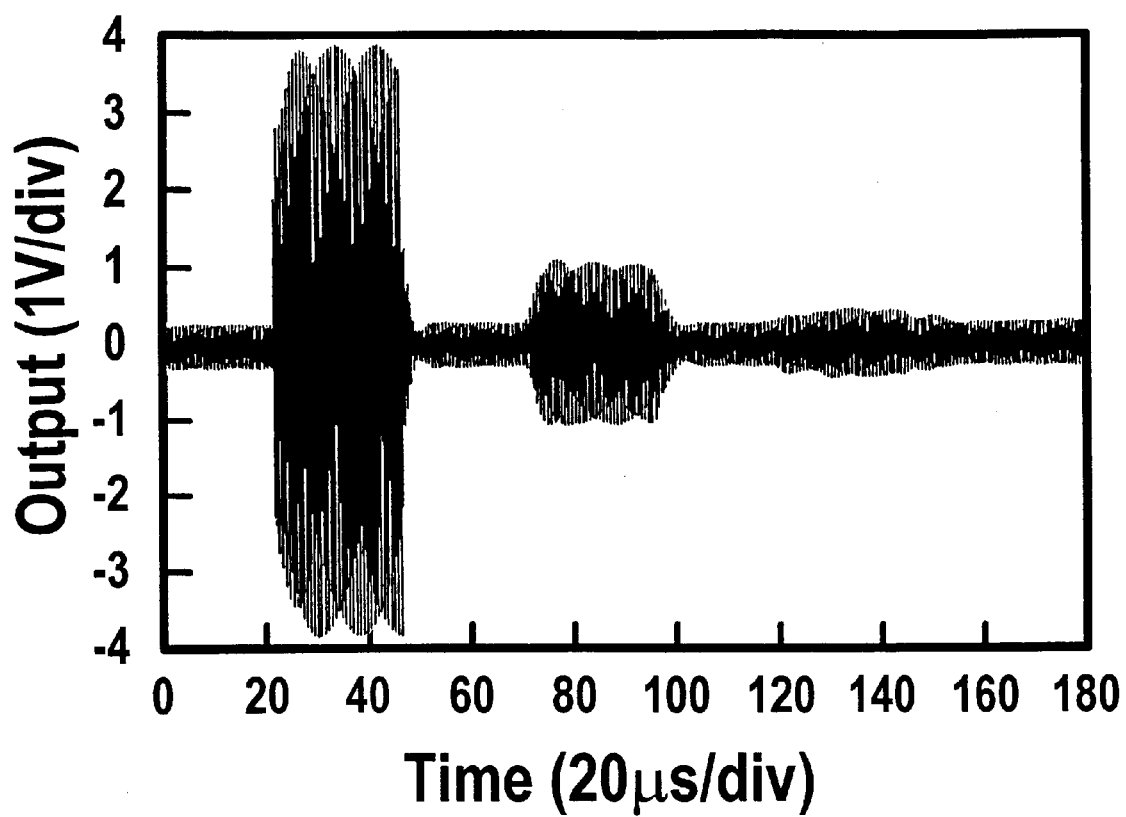
FIG. 13 shows an observed waveform at one of the carrier frequencies $f_i$ in the system for measuring sound velocity in material in FIG. 3.

FIG. 13 shows an observed waveform at one of the carrier frequencies $f_i$ in the system for measuring sound velocity in material in FIG. 3 under a condition that the input electric signals $E_i$ accompanied by the alternating current bias-signals $S_i$ are applied between first comb-shaped electrode 8A and counter electrode 3. The left- and right signal-parts correspond with those in FIG. 8, except that those in FIG. 13 are always accompanied by the alternating current bias-signals $S_i$. As a result, one of the alternating current bias-signals $S_i$ and the corresponding one of the delayed electric signals $D_i$ interfere directly with each other, so that the corresponding one of the interference signals $R_i$ with the corresponding one of the carrier frequencies $f_i$ occurs. In this time, the corresponding one of the interference signals $R_i$ has the maximum amplitude. Thus, for example, the alternating current bias-signal $S_4$ and the delayed electric signal $D_4$ interfere with each other, so that the interference signal $R_4$ with the carrier frequency $f_4$, occurs.

Figure 14:
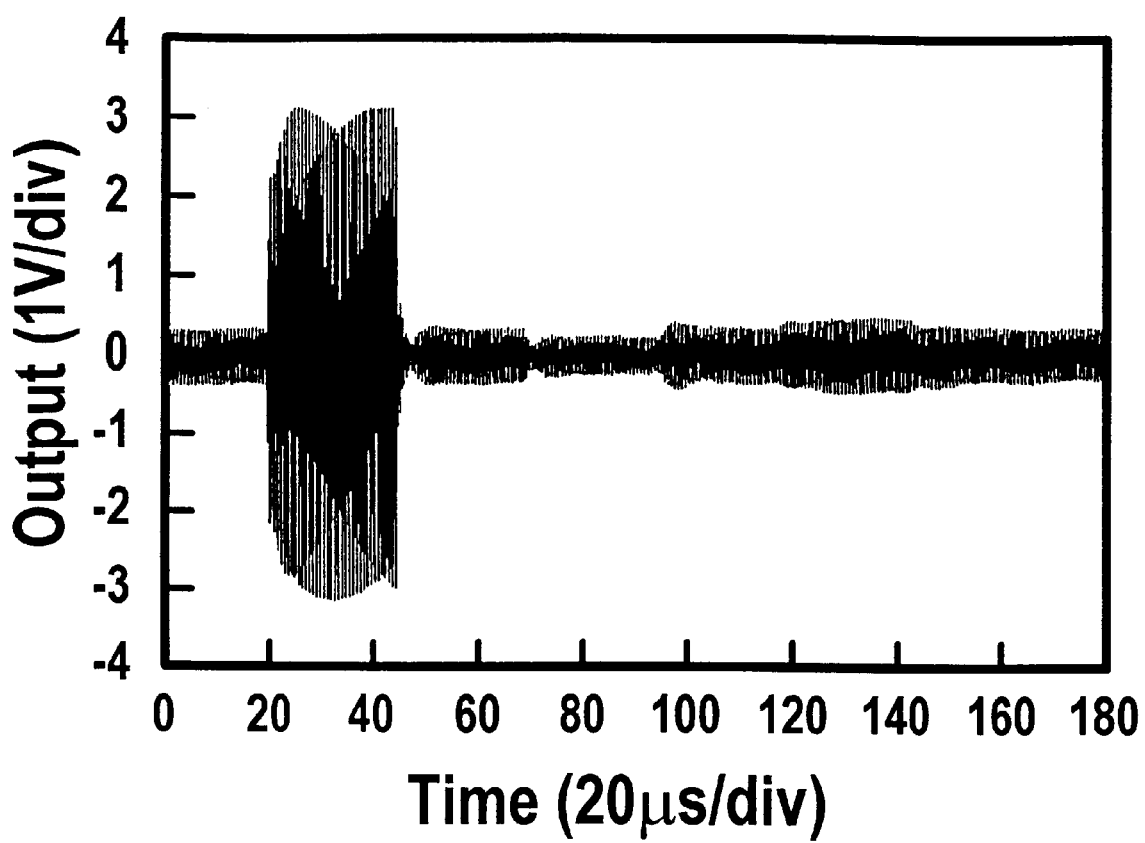
FIG. 14 shows an observed waveform at one of the carrier frequencies $f_i$ in the system for measuring sound velocity in material in FIG. 3.

FIG. 14 shows an observed waveform at one of the carrier frequencies $f_i$ in the system for measuring sound velocity in material in FIG. 3 under a condition that the input electric signals $E_i$ accompanied by the alternating current bias-signals $S_i$ are applied between first comb-shaped electrode 8A and counter electrode 3. In the same way as FIG. 13, for example, the alternating current bias-signal $S_8$ and the delayed electric signal $D_8$ interfere with each other, so that the interference signal $R_8$ with the carrier frequency $f_8$ occurs. In this time, the interference signal $R_8$ has the minimum amplitude in contrast to FIG. 13. Thus, there exists a minimum-amplitude zone corresponding with the right signal-part in FIG. 13.

Tracing a dependence of the amplitudes obtained from FIGS. 13 and 14, and other related data, on the carrier frequencies $f_i$ provides a distance between two neighboring peak amplitudes, that is, the frequency periodicity $\Delta f$ in the same way as FIG. 11.

Figure 15:
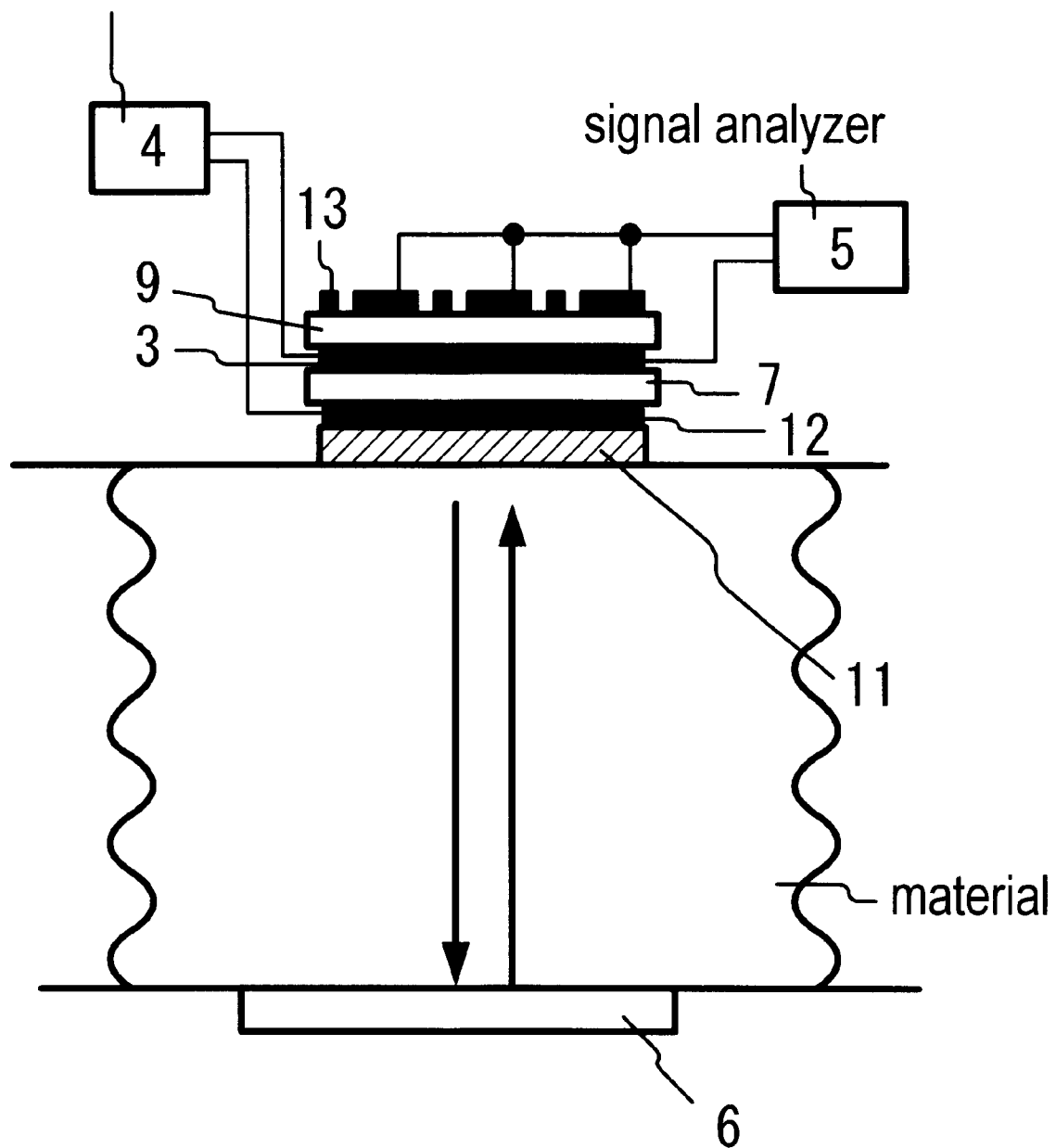
FIG. 15 shows a schematic illustration of a system for measuring sound velocity in material according to a third embodiment of the present invention.

FIG. 15 shows a schematic illustration of a system for measuring sound velocity in material according to a third embodiment of the present invention. The system for measuring sound velocity in material has the same construction as FIG. 3 except for the use of first interdigital arrangement 12 of two comb-shaped electrodes (12A and 12B) and second interdigital arrangement 13 of two comb-shaped electrodes (13A and 13B) in place of first interdigital arrangement 8 and second interdigital arrangement 10, respectively.

Figure 16:
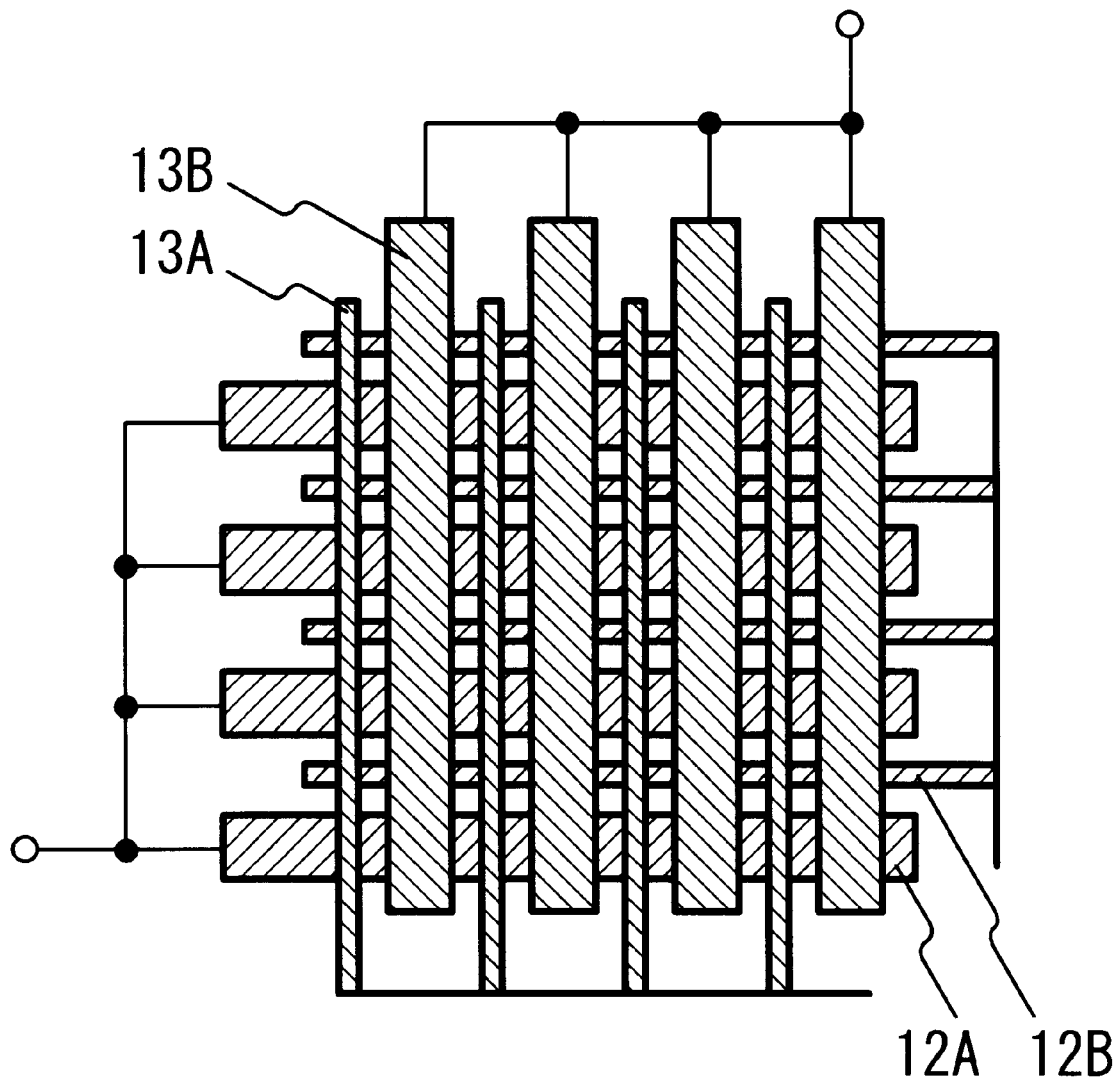
FIG. 16 shows a schematic illustration of first interdigital arrangement 12 and second interdigital arrangement 13 in the system for measuring sound velocity in material in FIG. 15.

FIG. 16 shows a schematic illustration of first interdigital arrangement 12 composed of first comb-shaped electrode 12A and second comb-shaped electrode 12B, and second interdigital arrangement 13 composed of first comb-shaped electrode 13A and second comb-shaped electrode 13B in the system for measuring sound velocity in material in FIG. 15.

The finger direction of first interdigital arrangement 12 is orthogonal to that of second interdigital arrangement 13. First interdigital arrangement 12, made of an aluminum thin film, has twenty electrode-finger pairs, a finger-overlap length (L) of 5 mm, and an interdigital periodicity (P) of 225 $\mu$m. First comb-shaped electrode 12A has a finger width ($W_A$) of 45 $\mu$m, and second comb-shaped electrode 12B has a finger width ($W_B$) of 12 $\mu$m Second interdigital arrangement 13 is made of the same material and has the same construction pattern as first interdigital arrangement 12 except that first comb-shaped electrode 14A has a finger width ($W_A$) of 12 $\mu$m, and second comb-shaped electrode 13B has a finger width ($W_B$) of 45 $\mu$m. First comb-shaped electrode 12A and second comb-shaped electrode 13B are connected with frequency-sweep oscillator 4 and frequency analyzer 5 in FIG. 15, respectively.

In the system for measuring sound velocity in material in FIG. 15, if the input electric signals $E_i$ from frequency-sweep oscillator 4 are applied between first comb-shaped electrode 12A and counter electrode 3 in turn, longitudinal waves along the direction vertical to the lower end surface of first piezoelectric substrate 7 are radiated into the material through silicone rubber 11. When the material is water, the condition of $P/T<4V_w/V_s$ enables a radiation of the longitudinal waves along the direction vertical to the lower end surface of first piezoelectric substrate 7 into water. In addition, the directionality of the longitudinal waves is sharper than that of the longitudinal wave in FIG. 3. In other words, a condition of $W_A/W_B$ in first interdigital arrangement 12 makes the directionality of the longitudinal wave sharper.

If the longitudinal waves are reflected at reflector 6 as shown in FIG. 15, reflected longitudinal waves are detected between second comb-shaped electrode 13B and counter electrode 3 as the delayed electric signals $D_i$, respectively. In this time, the directionality of the reflected longitudinal waves is sharper than that of the longitudinal waves radiated into the material, because the finger direction of first interdigital arrangement 12 is orthogonal to that of second interdigital arrangement 13. On the other hand, the electrical coupled-signals $C_i$ from the input electric signals $E_i$, respectively, are also detected between second comb-shaped electrode 13B and counter electrode 3. Thus, the electrical coupled-signals $C_i$ and the delayed electric signals $D_i$ interfere, respectively, so that the respective interference signals $R_i$ occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$. In addition, the sound velocity V is more precisely estimated than the system for measuring sound velocity in material in FIG. 3.

Figure 17:
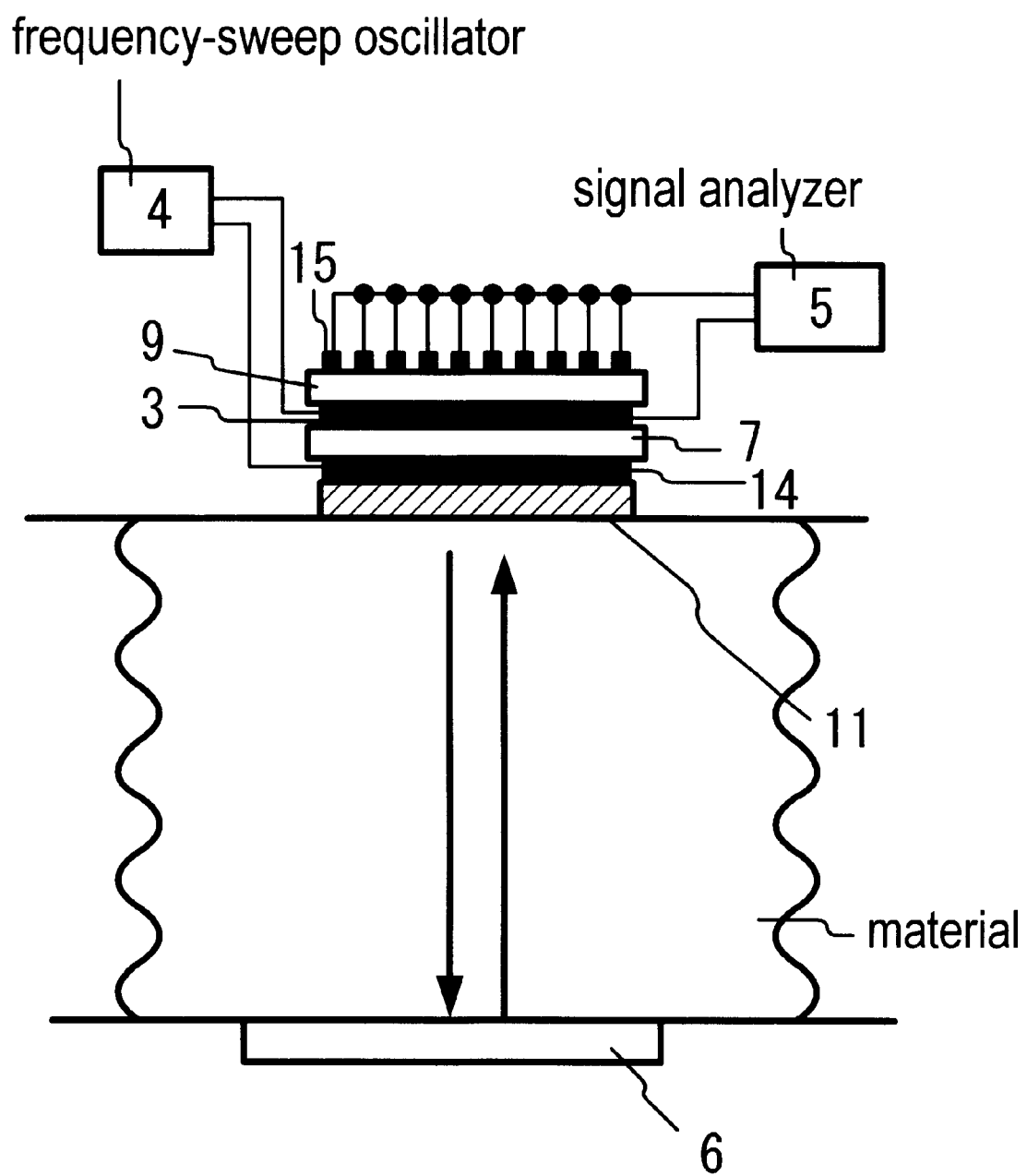
FIG. 17 shows a schematic illustration of a system for measuring sound velocity in material according to a fourth embodiment of the present invention.

FIG. 17 shows a schematic illustration of a system for measuring sound velocity in material according to a fourth embodiment of the present invention. The system for measuring sound velocity in material has the same construction as FIG. 3 except for the use of first comb-shaped electrode 14 and second comb-shaped electrode 15 in place of first interdigital arrangement 8 and second interdigital arrangement 10, respectively.

Figure 18:
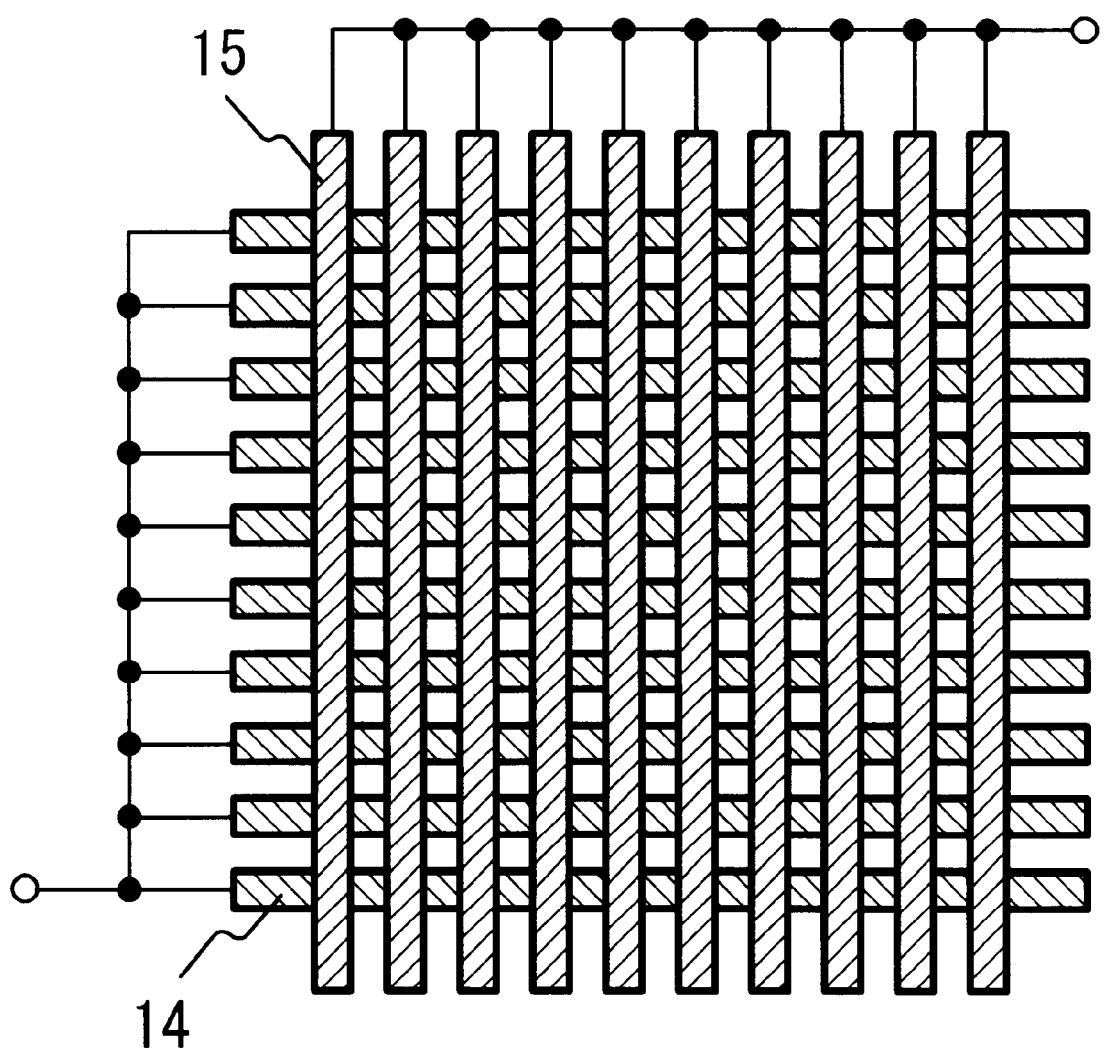
FIG. 18 shows a schematic illustration of first comb-shaped electrode 14 and second comb-shaped electrode 15.

FIG. 18 shows a schematic illustration of first comb-shaped electrode 14 and second comb-shaped electrode 15. First comb-shaped electrode 14 has forty electrode-fingers, a finger-overlap length (L) of 5 mm, a finger width (W) of 175 $\mu$m, and an interdigital periodicity (P) of 225 $\mu$m. Second comb-shaped electrode 15 has the same construction pattern as first comb-shaped electrode 14, of which the finger direction is orthogonal to that of second comb-shaped electrode 15.

In the system for measuring sound velocity in material in FIG. 17, if the input electric signals $E_i$ from frequency-sweep oscillator 4 are applied between first comb-shaped electrode 14 and counter electrode 3 in turn, longitudinal waves along the direction vertical to the lower end surface of first piezoelectric substrate 7 are radiated into the material through silicone rubber 11. When the material is water, the condition of $P/T<4V_w/V_s$ enables a radiation of the longitudinal waves along the direction vertical to the lower end surface of first piezoelectric substrate 7 into water.

If the longitudinal waves are reflected at reflector 6 as shown in FIG. 17, reflected longitudinal waves are detected between second comb-shaped electrode 15 and counter electrode 3 as the delayed electric signals $D_i$, respectively. On the other hand, the electrical coupled-signals $C_i$ from the input electric signals $E_i$, respectively, are also detected between second comb-shaped electrode 15 and counter electrode 3. Thus, the electrical coupled-signals $C_i$ and the delayed electric signals $D_i$ interfere, respectively, so that the respective interference signals $R_i$ occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$.

In the system for measuring sound velocity in material in FIG. 15 or 17, if the input electric signals $E_i$ accompanied by the alternating current bias-signals $S_i$ with the carrier frequencies $f_i$, respectively, are provided from frequency-sweep oscillator 4, the alternating current bias-signals $S_i$ and the delayed electric signals $D_i$ interfere respectively with each other. As a result, the respective interference signals $R_i$ occur. Tracing a dependence of respective amplitudes of the interference signals $R_i$ on the carrier frequencies $f_i$ provides a frequency periodicity $\Delta f$. Thus, a sound velocity V in the material is estimated from the frequency periodicity $\Delta f$. The use of the pulse-modulated signals accompanied by the alternating current bias-signals $S_i$ enables a more stable operation.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A system for measuring sound velocity in material comprising:

a piezoelectric substrate;

a first comb-shaped electrode formed on an upper end surface of said piezoelectric substrate;

a second comb-shaped electrode formed on said upper end surface of said piezoelectric substrate;

a counter electrode formed on a lower end surface of said piezoelectric substrate and in contact with a surface-part of a material;

a frequency-sweep oscillator generating input electric signals $E_i$ (i=1, 2, . . . , n) with carrier frequencies $f_i$ (i=1, 2, . . . , n), respectively; and a frequency analyzer, said first- and second comb-shaped electrodes forming an interdigital arrangement, said first comb-shaped electrode and said counter electrode receiving said input electric signals $E_i$ in turn, radiating longitudinal waves into said material along the direction vertical to said lower end surface of said piezoelectric substrate, and making the opposite surface-part of said material reflect said longitudinal waves back, said second comb-shaped electrode and said counter electrode detecting electrical coupled-signals $C_i$ (i=1, 2, ..., n) from said input electric signals $E_i$, respectively, as well as reflected longitudinal waves as delayed electric signals $D_i$ (i=1, 2, ..., n), respectively, said frequency analyzer causing said electrical coupled-signals $C_i$ and said delayed electric signals $D_i$ to interfere respectively, making respective interference signals $R_i$ (i=1, 2, ..., n), detecting respective amplitudes of said interference signals $R_i$, clarifying a frequency periodicity $\Delta f$ from a dependence of said amplitudes on said carrier frequencies $f_i$, and calculating a sound velocity V in said material from the product of said frequency periodicity $\Delta f$ and twice a distance Z between said piezoelectric substrate and said opposite surface-part of said material.

2. A system for measuring sound velocity in material as defined in claim 1 further comprising a reflector, which is parallel with said lower end surface of said piezoelectric substrate and in contact with said opposite surface-part of said material.

3. A system for measuring sound velocity in material as defined in claim 1, wherein the ratio of the interdigital periodicity of said interdigital arrangement to the thickness of said piezoelectric substrate is smaller than four times the ratio of the longitudinal wave velocity in said material to the longitudinal wave velocity in said piezoelectric substrate.

4. A system for measuring sound velocity in material as defined in claim 1, wherein increasing the number of electrode-finger pairs in said interdigital arrangement makes the directionality of said longitudinal waves sharper under a condition that the total amount of all the finger-areas of said first comb-shaped electrode is constant.

5. A system for measuring sound velocity in material as defined in claim 1, wherein said material is a liquid matter.

6. A system for measuring sound velocity in material as defined in claim 1, wherein said material is a cellular tissue.

7. A system for measuring sound velocity in material as defined in claim 1 further comprising a polymer film, with which said lower end surface of said counter electrode is coated.

8. A system for measuring sound velocity in material as defined in claim 1, wherein:

said input electric signals $E_i$ is accompanied by alternating current bias-signals $S_i$ (i=1, 2, ..., n) with said carrier frequencies $f_i$, respectively; and said frequency analyzer causes, not said electrical coupled-signals $C_i$, but said alternating current bias-signals $S_i$, and said delayed electric signals $D_i$ to interfere respectively, and makes said interference signals $R_i$.

9. A system for measuring sound velocity in material comprising:

a first piezoelectric substrate;

a first interdigital arrangement of two comb-shaped electrodes formed on a lower end surface of said first piezoelectric substrate, a lower end surface of said first interdigital arrangement being in contact with a surface-part of a material;

a second piezoelectric substrate;

a second interdigital arrangement of two comb-shaped electrodes formed on an upper end surface of said second piezoelectric substrate;

a counter electrode cemented between said first- and second piezoelectric substrates;

a frequency-sweep oscillator generating input electric signals $E_i$ (i=1, 2, ..., n) with carrier frequencies $f_i$ (i=1, 2, ..., n), respectively; and a frequency analyzer, one of said two comb-shaped electrodes in said first interdigital arrangement and said counter electrode receiving said input electric signals $E_i$ in turn, radiating longitudinal waves into said material along the direction vertical to said lower end surface of said first piezoelectric substrate, and making the opposite surface-part of said material reflect said longitudinal waves back, one of said two comb-shaped electrodes in said second interdigital arrangement and said counter electrode detecting electrical coupled-signals $C_i$ (i=1, 2, ..., n) from said input electric signals $E_i$, respectively, as well as reflected longitudinal waves as delayed electric signals $D_i$ (i=1, 2, ..., n), respectively, said frequency analyzer causing said electrical coupled-signals $C_i$ and said delayed electric signals $D_i$ to interfere respectively, making respective interference signals $R_i$ (i=1, 2, ..., n), detecting respective amplitudes of said interference signals $R_i$, clarifying a frequency periodicity $\Delta f$ from a dependence of said amplitudes on said carrier frequencies $f_i$, and estimating a sound velocity V in said material from said frequency periodicity $\Delta f$.

10. A system for measuring sound velocity in material as defined in claim 9, wherein the finger direction of said second interdigital arrangement is orthogonal to that of said first interdigital arrangement.

11. A system for measuring sound velocity in material as defined in claim 9, wherein the finger width in said one of said two comb-shaped electrodes in said first interdigital arrangement is wider than that in the other of said two comb-shaped electrodes in said first interdigital arrangement, and the finger width in said one of said two comb-shaped electrodes in said second interdigital arrangement is wider than that in the other of said two comb-shaped electrodes in said second interdigital arrangement.

12. A system for measuring sound velocity in material as defined in claim 9 further comprising a reflector, which is parallel with said lower end surface of said first piezoelectric substrate and in contact with said opposite surface-part of said material.

13. A system for measuring sound velocity in material as defined in claim 9, wherein the ratio of the interdigital periodicity of said first interdigital arrangement to the thickness of said first piezoelectric substrate is smaller than four times the ratio of the longitudinal wave velocity in said material to the longitudinal wave velocity in said first piezoelectric substrate.

14. A system for measuring sound velocity in material as defined in claim 9, wherein increasing the number of electrode-finger pairs in said first interdigital arrangement makes the directionality of said longitudinal waves sharper under a condition that the total amount of all the finger-areas of said one of said two comb-shaped electrodes in said first interdigital arrangement is constant.

15. A system for measuring sound velocity in material as defined in claim 9, wherein:

said input electric signals $E_i$ is accompanied by alternating current bias-signals $S_i$ (i=1, 2, ..., n) with said carrier frequencies $f_i$, respectively; and said frequency analyzer causes, not said electrical coupled-signals $C_i$, but said alternating current bias-signals $S_i$, and said delayed electric signals $D_i$ to interfere respectively, and makes said interference signals $R_i$.

16. A system for measuring sound velocity in material comprising:

a first piezoelectric substrate;

a first comb-shaped electrode formed on a lower end surface of said first piezoelectric substrate, a lower end surface of said first comb-shaped electrode being in contact with a surface-part of a material;

a second piezoelectric substrate;

a second comb-shaped electrode formed on an upper end surface of said second piezoelectric substrate;

a counter electrode cemented between said first- and second piezoelectric substrates;

a frequency-sweep oscillator generating input electric signals $E_i$ (i=1, 2, . . . , n) with carrier frequencies $f_i$ (i=1, 2, . . . , n), respectively; and a frequency analyzer, said first comb-shaped electrode and said counter electrode receiving said input electric signals $E_i$ in turn, radiating longitudinal waves into said material along the direction vertical to said lower end surface of said first piezoelectric substrate, and making the opposite surface-part of said material reflect said longitudinal waves back, said second comb-shaped electrode and said counter electrode detecting electrical coupled-signals $C_i$ (i=1, 2, . . . , n) from said input electric signals $E_i$, respectively, as well as reflected longitudinal waves as delayed electric signals $D_i$ (i=1, 2, . . . , n), respectively, said frequency analyzer causing said electrical coupled-signals $C_i$ and said delayed electric signals $D_i$ to interfere respectively, making respective interference signals $R_i$ (i=1, 2, . . . , n), detecting respective amplitudes of said interference signals $R_i$, clarifying a frequency periodicity $\Delta f$ from a dependence of said amplitudes on said carrier frequencies $f_i$, and estimating a sound velocity V in said material from said frequency periodicity $\Delta f$.

17. A system for measuring sound velocity in material as defined in claim 16, wherein the finger direction of said second comb-shaped electrode is orthogonal to that of said first comb-shaped electrode.

18. A system for measuring sound velocity in material as defined in claim 16 further comprising a reflector, which is parallel with said lower end surface of said first piezoelectric substrate and in contact with said opposite surface-part of said material.

19. A system for measuring sound velocity in material as defined in claim 16, wherein the ratio of the interdigital periodicity of said first comb-shaped electrode to the thickness of said first piezoelectric substrate is smaller than four times the ratio of the longitudinal wave velocity in said material to the longitudinal wave velocity in said first piezoelectric substrate.

20. A system for measuring sound velocity in material as defined in claim 16, wherein increasing the number of electrode-finger pairs in said first comb-shaped electrode makes the directionality of said longitudinal waves sharper under a condition that the total amount of all the finger-areas of said first comb-shaped electrode is constant.

21. A system for measuring sound velocity in material as defined in claim 16, wherein:

said input electric signals $E_i$ is accompanied by alternating current bias-signals $S_i$ (i=1, 2, . . . , n) with said carrier frequencies $f_i$, respectively; and said frequency analyzer causes, not said electrical coupled-signals $C_i$, but said alternating current bias-signals $S_i$, and said delayed electric signals $D_i$ to interfere respectively, and makes said interference signals $R_i$.

* * * * *